(12) United States Patent
Koulikov et al.

(10) Patent No.: US 9,678,003 B2
(45) Date of Patent: Jun. 13, 2017

(54) CAVITY ENHANCED LASER BASED ISOTOPIC GAS ANALYZER

(71) Applicants: Serguei Koulikov, Mountain View, CA (US); Alexander Kachanov, San Jose, CA (US)

(72) Inventors: Serguei Koulikov, Mountain View, CA (US); Alexander Kachanov, San Jose, CA (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

(21) Appl. No.: 14/156,842

(22) Filed: Jan. 16, 2014

(65) Prior Publication Data
US 2014/0192347 A1 Jul. 10, 2014

Related U.S. Application Data (63) Continuation of application No. 13/538,620, filed on Jun. 29, 2012, now Pat. No. 8,665,442.
(Continued)

(51) Int. Cl.
*G01N 21/00* (2006.01)
*G01N 21/39* (2006.01)
(Continued)

(52) U.S. Cl.
CPC ............ *G01N 21/39* (2013.01); *G01J 3/4338* (2013.01); *G01N 21/1702* (2013.01);
(Continued)

(58) Field of Classification Search
CPC ........ G01N 21/39; G01N 21/3504; G01J 3/42
See application file for complete search history.

(56) References Cited

U.S. PATENT DOCUMENTS

| 3,869,210 A | 3/1975 | Fletcher et al. |
| 3,938,365 A | 2/1976 | Dewey |

(Continued)

FOREIGN PATENT DOCUMENTS

| JP | 07-270308 A | 10/1995 |
| WO | WO 2007/004168 A1 | 1/2007 |

(Continued)

OTHER PUBLICATIONS

Burggraf et al., "Quantitative Photoacoustic Spectroscopy of Intensely Light-Scattering Thermally Thick Samples," Anal. Chem., 1981, vol. 53, pp. 759-764.
(Continued)

*Primary Examiner* — Michael A Lyons
(74) *Attorney, Agent, or Firm* — Leydig, Voit & Mayer, Ltd; Gerald T. Gray (57) ABSTRACT

Systems and methods for measuring the isotope ratio of one or more trace gases and/or components of gas mixtures such as different gas species present in a gas mixture. The system includes a resonant optical cavity having two or more mirrors and containing a gas, the cavity having a free spectral range that equals the difference between frequencies of two measured absorption lines of different gas species in the gas, or of two different isotopes, divided onto an integer number. The system also includes a continuous-wave tunable laser optically coupled with the resonant optical cavity, and a detector system for measuring an absorption of laser light by the gas in the cavity. The detector system includes one of a photo-detector configured to measure an intensity of the intra-cavity light or both a photo-acoustic sensor configured to measure photo-acoustic waves generated in the cavity and a photo-detector configured to measure an intensity of the intra-cavity light.

15 Claims, 7 Drawing Sheets

Related U.S. Application Data (60) Provisional application No. 61/524,911, filed on Aug. 18, 2011.

(51) Int. Cl.
  *G01N 21/17* (2006.01)
  *G01J 3/433* (2006.01)
  *G01N 29/24* (2006.01)
  *G01N 21/61* (2006.01)
  *G01N 21/59* (2006.01)

(52) U.S. Cl.
  CPC ............ *G01N 21/59* (2013.01); *G01N 21/61* (2013.01); *G01N 29/2425* (2013.01); *G01N 2021/1704* (2013.01); *G01N 2201/023* (2013.01); *G01N 2201/06113* (2013.01); *G01N 2291/021* (2013.01)

(56) References Cited

U.S. PATENT DOCUMENTS

| | | | |
|---|---|---|---|
| 4,011,013 A | 3/1977 | Barrett | |
| 4,733,397 A | 3/1988 | Gallagher et al. | |
| 4,793,709 A | 12/1988 | Jabr et al. | |
| 4,958,921 A | 9/1990 | Early | |
| 5,260,663 A | 11/1993 | Blades | |
| 5,313,270 A | 5/1994 | Fishman et al. | |
| 5,432,610 A | 7/1995 | King et al. | |
| 5,452,084 A | 9/1995 | Mitchell et al. | |
| 5,528,040 A | 6/1996 | Lehmann et al. | |
| 5,544,186 A | 8/1996 | Sauer et al. | |
| 5,621,744 A | 4/1997 | Kikuchi et al. | |
| 5,790,259 A | 8/1998 | Mizuhata et al. | |
| 5,912,740 A | 6/1999 | Zare et al. | |
| 5,929,981 A | 7/1999 | Keilbach | |
| 5,973,864 A | 10/1999 | Lehmann et al. | |
| 5,999,547 A | 12/1999 | Schneider et al. | |
| 6,084,682 A | 7/2000 | Zare | |
| 6,205,159 B1 | 3/2001 | Sesko et al. | |
| 6,233,052 B1 | 5/2001 | Zare et al. | |
| 6,323,481 B2 | 11/2001 | Ueki | |
| 6,421,130 B1 | 7/2002 | Phillion | |
| 6,455,829 B1 | 9/2002 | Fukumura | |
| 6,466,322 B1 | 10/2002 | Paldus et al. | |
| 6,504,145 B1 | 1/2003 | Romanini et al. | |
| 6,608,683 B1 | 8/2003 | Pilgrim et al. | |
| 6,618,148 B1 | 9/2003 | Pilgrim et al. | |
| 7,012,696 B2 | 3/2006 | Orr et al. | |
| 7,069,769 B2 | 7/2006 | Kung | |
| 7,098,441 B2 | 8/2006 | Yamaguchi et al. | |
| 7,245,380 B2 | 7/2007 | Kosterev | |
| 7,259,856 B2 | 8/2007 | Kachanov et al. | |
| 7,263,871 B2 | 9/2007 | Selker et al. | |
| 7,398,672 B2 | 7/2008 | Riddle | |
| 7,450,240 B2 | 11/2008 | Morville et al. | |
| 7,535,573 B2 | 5/2009 | Kachanov et al. | |
| 7,569,823 B2 | 8/2009 | Miller | |
| 7,612,885 B2 | 11/2009 | Cole et al. | |
| 7,639,373 B2 | 12/2009 | Torii et al. | |
| 7,663,756 B2 | 2/2010 | Cole | |
| 7,679,750 B2 | 3/2010 | Li et al. | |
| 7,765,871 B2 | 8/2010 | Riddle | |
| 7,805,980 B2 | 10/2010 | Kosterev | |
| 7,902,534 B2 | 3/2011 | Cole et al. | |
| 8,675,209 B2 | 3/2014 | Usami | |
| 9,116,047 B2 | 8/2015 | Koulikov | |
| 2002/0097402 A1 | 7/2002 | Manning | |
| 2002/0134909 A1 | 9/2002 | Shiota et al. | |
| 2003/0043377 A1 | 3/2003 | Balobeck | |
| 2003/0189711 A1* | 10/2003 | Orr et al. | 356/484 |
| 2004/0065816 A1 | 4/2004 | Ye et al. | |
| 2006/0084180 A1 | 4/2006 | Paldus et al. | |
| 2006/0119851 A1 | 6/2006 | Bounaix | |
| 2006/0123884 A1 | 6/2006 | Selker et al. | |
| 2008/0111993 A1 | 5/2008 | Miller | |
| 2008/0134756 A1 | 6/2008 | Riddle | |
| 2008/0151248 A1 | 6/2008 | Cole et al. | |
| 2008/0196477 A1 | 8/2008 | Van Herpen | |
| 2009/0229345 A1 | 9/2009 | Van Kesteren | |
| 2009/0249861 A1 | 10/2009 | Van Dijk et al. | |
| 2009/0288474 A1 | 11/2009 | Kalkman et al. | |
| 2010/0002234 A1 | 1/2010 | Cormier et al. | |
| 2010/0011836 A1 | 1/2010 | Kalkman et al. | |
| 2010/0296095 A1 | 11/2010 | Hong et al. | |
| 2011/0214479 A1 | 9/2011 | Kachanov et al. | |
| 2011/0295140 A1* | 12/2011 | Zaidi et al. | 600/532 |
| 2012/0154807 A1 | 6/2012 | Usami | |
| 2013/0050706 A1 | 2/2013 | Koulikov | |
| 2013/0100973 A1 | 4/2013 | Bondu et al. | |

FOREIGN PATENT DOCUMENTS

| | | |
|---|---|---|
| WO | WO 2008/026189 A1 | 3/2008 |
| WO | WO 2011109557 A | 9/2011 |

OTHER PUBLICATIONS

Cermak, Peter et al., "Optical-Feedback Cavity-Enhanced Absorption Spectroscopy Using a Short-Cavity Vertical-External-Cavity Surface-Emitting Laser," IEEE Photonics Technology Letters, IEEE Service Center, Piscataway, NJ, US, (2010), vol. 22, No. 21, pp. 1607-1609.

Clairon, A. et al., "Frequency Noise Analysis of Optically Self-Locked Diode Lasers," IEEE J. Quantum Electronics, 25(6):1131-1142 (1989).

Courtillot, I. et al., "Sub-ppb $NO_2$ detection by optical feedback cavity-enhanced absorption spectroscopy with a blue diode laser," Applied Physics B, (2006), vol. 85, No. 2-3, pp. 407-412.

Crosson, Eric R. et al., "Stable Isotope Ratios Using Cavity Ring-Down Spectroscopy: Determination of 13C/12C for Carbon Dioxide in Human Breath," Analytical Chemistry, May 1, 2002, vol. 74, No. 9, pp. 2003-2007.

Hamilton, D. J. et al., "A quantum cascade laser-based optical feedback cavity-enhanced absorption spectrometer for the simultaneous measurement of $CH_4$ and $N_2O$ in air," Applied Physics B, (2011), vol. 102, No. 4, pp. 879-890.

Hippler et al., "Cavity-enhanced resonant photoacoustic spectroscopy with optical feedback cw diode lasers: A novel technique for ultratrace gas analysis and high-resolution spectroscopy," The Journal of Chemical Physics, 2010, vol. 133, pp. 044308-1-044308-8.

Kosterev, A. A. et al., "Quartz-enhanced photoacoustic spectroscopy," Optics Letters 27(21):1902-1904 (Nov. 1, 2002).

Kosterev, A. A. et al., "Trace Humidity Sensor based on Quartz-Enhanced Photoacoustic Spectroscopy," Lacsea 2006, Incline Village, NV, Feb. 5-9, 2006.

Morville, J. et al., "Trace gas detection with DFB lasers and cavity ring-down spectroscopy," SPIE Proc., (2002), vol. 4485, pp. 236-243.

Morville, J. et al., "Effects of laser phase noise on the injection of a high-finesse cavity," Applied Optics, (2002), vol. 41, No. 33, pp. 6980-6990.

Morville, J. et al., "Two schemes for trace detection using cavity ringdown spectroscopy," Applied Physics B, (2004), vol. 78, pp. 465-476.

Morville, J. et al., "Fast, low-noise, mode-by-mode, cavity-enhanced absorption spectroscopy by diode-laser self-locking," Applied Physics B, (2005), vol. 80, No. 8, pp. 1027-1038.

Motto-Ros, V. et al., "Extensive characterization of optical feedback cavity enhanced absorption spectroscopy (OF-CEAS) technique: ringdown-time calibration of the absorption scale," Applied Physics B, (2008), vol. 91, No. 1, pp. 203-211.

Romanini, D. et al., "CW cavity ring down spectroscopy," Chemical Physics Letters, (1997), 264, pp. 316-322.

Romanini, D. et al., "Diode laser cavity ring down spectroscopy," Chemical Physics Letters, (1997), 270, pp. 538-545.

Romanini, D. et al., "Measurement of trace gases by diode laser cavity ringdown spectroscopy," Proc. SPIE EUROPTO (Ser. Environmental Sensing), (1999), vol. 3821, pp. 94-104.

(56) References Cited

OTHER PUBLICATIONS

Rossi, A. et al., "Optical enhancement of diode laser-photoacoustic trace gas detection by means of external Fabry-Perot cavity," Appl. Phys. Lett. 87, 041110 (2005).
Wehr, R. et al., "Optical feedback cavity-enhanced absorption spectroscopy for in situ measurements of the ratio 13C: 12C in CO2," Applied Physics B, (2008), vol. 92, No. 3, pp. 459-465.
International Search Report and Written Opinion for PCT/US2012/051267 dated Dec. 12, 2012.
Wahl et al., "Applications of Cavity Ring-Down Spectroscopy to High Precision Isotope Ratio Measurement of 13C/12C in Carbon Dioxide", Isotopes in Environmental and Health Studies, col. 42, No. 1, Mar. 2006 (Mar. 2006), pp. 21-35.
Wang et al., "A Novel Multiple Species Ringdown Spectrometer for in Situ Measurements of Methane, Carbon dioxide, and Carbon Isotope", Applied Physics b; Lasers and Optics, Springer, Berlin, DE, vol. 92, No. 2, Jun. 25, 2008 (Jun. 25, 2008), pp. 259-270.
European Search Report, 12823968.8, performed within the European Patent Office on Apr. 7, 2015.
Owens, James C., "Optical Refractive Index of Air: Dependence on Pressure, Temperature and Composition," Applied Optics, Jan. 1967, vol. 6, No. 1, pp. 51-59.
Rentschler, Harvey Clayton, "A New Method for Measuring the Index of Refraction of a Gas for Different Light-waves and Results Obtained for Several Gases," The Astrophysical Journal, Dec. 1908, vol. 28, No. 5, pp. 345-359.
Zucker, Michael E. et al., "Measurement of Optical Path Fluctuations due to Residual Gas in the LIGO 40 Meter Interferometer," Proceedings of the Seventh Marcel Grossman Meeting on recent developments in theoretical and experimental general relativity, gravitation, and relativistic field theories. Proceedings of the Meeting held at Stanford University, Jul. 24-30, 1994. Edited by Robert T. Jantzen, G. Mac Keiser, and Remo Ruffini, River Edge, New Jersey: World Scientific, 1996., p. 1434.
European Patent Office, International Search Report and the Written Opinion in International Patent Application No. PCT/US2014/059966 (Jan. 15, 2015).

\* cited by examiner

CAVITY ENHANCED LASER BASED ISOTOPIC GAS ANALYZER

CROSS-REFERENCES TO RELATED APPLICATIONS

This application is a continuation application of U.S. Non-provisional application Ser. No. 13/538,620, filed Jun. 29, 2012, which claims the benefit of, and priority to, U.S. provisional Patent application No. 61/524,911, filed Aug. 18, 2011, the contents of both of which are hereby incorporated by reference.

BACKGROUND

The present invention relates generally to trace gas detection and more specifically to cavity enhanced absorption spectroscopy systems and methods.

Optical absorption spectroscopy involves passing radiation through a sample, e.g., an analyte, an inferring properties of the sample from measurements performed on the radiation. For example, trace gas detection can be spectroscopically performed by taking measurements to detect the presence or absence of spectral absorption lines corresponding to the gas species of interest. Spectroscopic analysis of isotopes can also be performed. However, because the integral line intensities of absorption gas lines are sensitive to the gas temperature, and the pressure broadening of those lines is sensitive to the gas pressure and the gas composition, measurements of the isotopic ratio with high accuracy require measuring of the analyzed gas temperature and pressure with high accuracy, and measuring of the composition of major components of the analyzed gas. Moreover, because a measurement of the isotopic ratio very often requires working at low gas pressure, when gas absorption lines are narrow and their mutual overlapping decreased, it can be very hard to precisely measure the integral intensities of the absorption lines. Such measurements of the integral intensities require very precise measurements of laser frequency.

Accordingly it is desirable to provide improved spectroscopy systems and methods for measuring gas species and/or isotopes.

SUMMARY

The present invention provides systems and methods for measuring the isotope ratio of one or more trace gases and/or components of gas mixtures such as different gas species present in a gas mixture.

Embodiments of the present invention provide systems and devices for detecting the isotopic ratio of the analyzed gas with high accuracy using a resonance optical cavity, which contains a gas mixture to be analyzed, a laser coupled to the cavity, and a light sensitive detector. The optical cavity can include any type of cavity with two or more cavity mirrors, including a linear or a ring cavity. A laser that is capable of being frequency-scanned is coupled to the cavity though one of the cavity mirrors (i.e., the cavity coupling mirror). A detection method can be based on any of a variety of cavity enhanced optical spectroscopy (CEOS) methods, for example, cavity ring-down spectroscopy (CRDS) methods, cavity phase shift spectroscopy methods, cavity enhanced absorption spectroscopy (CEAS) methods, or cavity enhanced photo-acoustic spectroscopy (CE-PAS) methods (see, e.g., U.S. patent application Ser. No. 12/660,614, (US Published Patent application 2011-0214479 A1) filed on Mar. 2, 2010, entitled "METHOD AND APPARATUS FOR THE PHOTO-ACOUSTIC IDENTIFICATION AND QUANTIFICATION OF ANALYTE SPECIES IN A GASEOUS OR LIQUID MEDIUM", the contents of which are hereby incorporated by reference).

Because the integral line intensities of gas absorption lines are sensitive to the gas temperature, and the pressure broadening of those lines is sensitive to the gas pressure and the gas composition, measurements of the isotopic ratio with high accuracy require measuring of the analyzed gas temperature and pressure with high accuracy, and measuring of the composition of major components of the analyzed gas. Moreover, because a measurement of the isotopic ratio very often requires working at low gas pressure, when gas absorption lines are narrow and their mutual overlapping decreased, it can be very hard to precisely measure the integral intensities of the absorption lines. Such measurements of the integral intensities require very precise measurements of laser frequency. The task is simplified if the measurements of the peak intensities provide the required accuracy.

Figure 1:
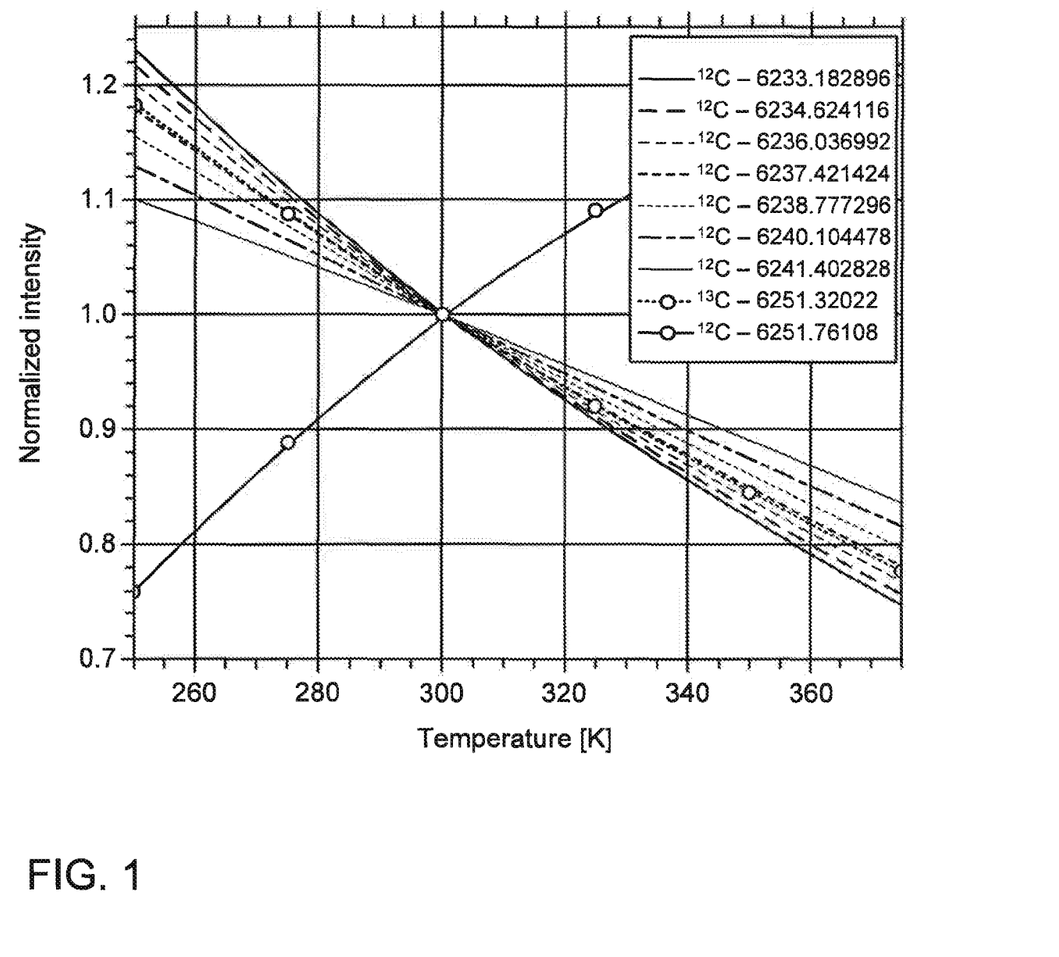
FIG. 1 illustrates temperature dependences of the R (6), R (36), R (8), R (10), R (12), R (14), R (16), R (18), and R (36) lines of 12C16O16O and the R(12) line of 13C16O16O for the (3,00,1)-(0,00,0) combination band of carbon dioxide. The graph shows that the temperature dependences of the integral intensities of lines with different quantum numbers are quite different.
Figure 2:
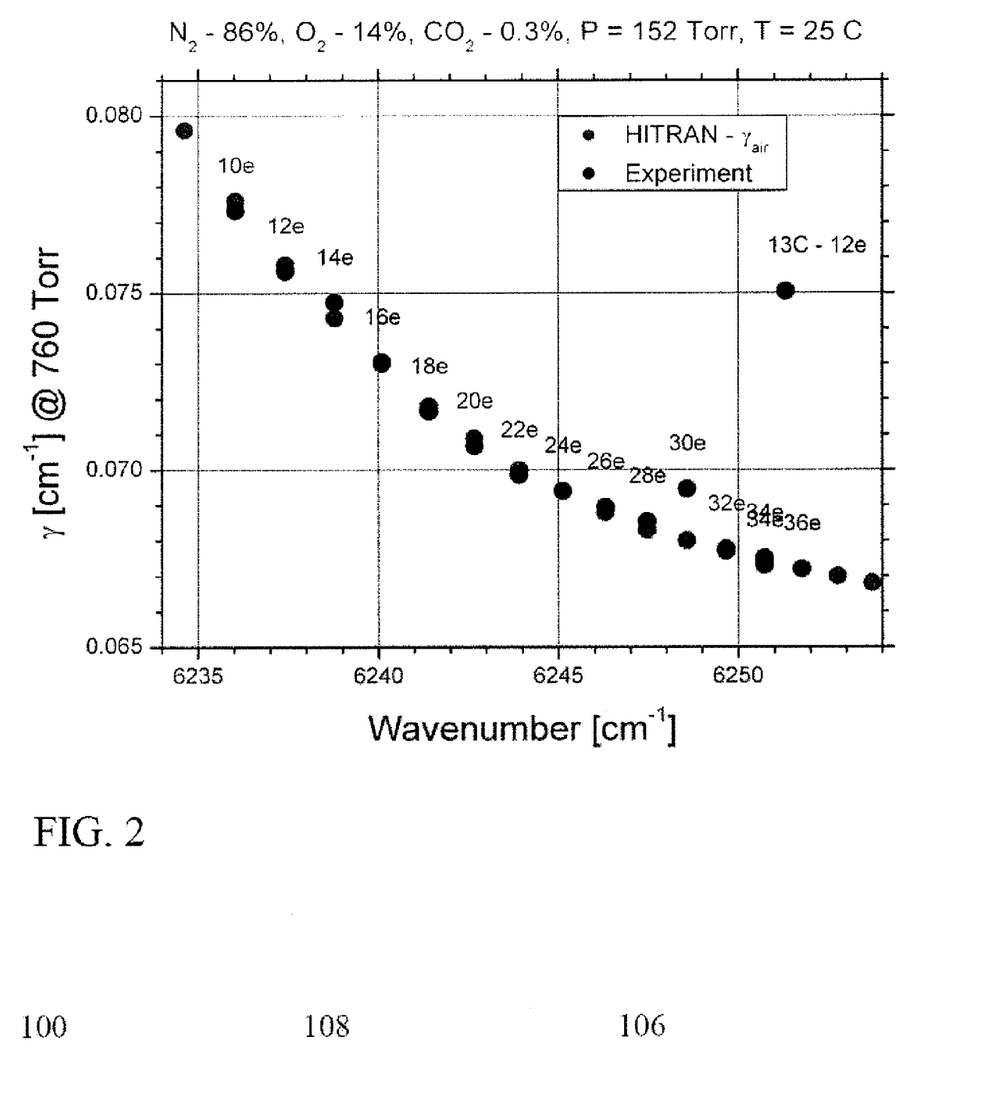
FIG. 2 illustrates HITRAN's and experimental parameters of the pressure broadening of different lines of $CO_2$ having different quantum numbers. The graph shows that the pressure broadening coefficients are similar for lines which belong to two different isotopes, but with the same quantum numbers.

The approach of one embodiment is based on the fact that absorption lines of different isotopes may have similar temperature dependences and pressure broadening coefficients, particularly isotopes having close quantum numbers as shown in FIGS. 1 and 2. So, if two lines of different isotopes with close quantum numbers are chosen, then instead of measuring the ratio of integral intensities of the corresponding lines their peak intensities are measured. However, if it is still necessary to measure their integral intensities, this can be done by a synchronous scanning the cavity modes through both spectroscopic features. The synchronous measurements of the integral intensities of both lines will be more accurate because two lines have close pressure broadening parameters.

Embodiments of the present invention allow for replacing the more complex measurements of the line area (i.e., integral intensity) with simpler measurements of the peak height, which is possible if the lines of two isotopologues react to the ambient condition changes in the same or a similar way. Using close or similar quantum numbers will also help if the integral line intensities are measured and compared.

According to an embodiment, a gas analyzer system is provided for measuring a concentration of two or more components in a gas mixture. The system typically includes a resonant optical cavity having two or more mirrors and containing a gas having chemical species to be measured, the cavity having a free spectral range that equals the difference between frequencies of two measured absorption lines of different gas species divided onto an integer number. The system also typically includes a continuous-wave tunable laser optically coupled with the resonant optical cavity, and a detector system for measuring an absorption of laser light by the gas in the cavity. In certain aspects, the gas analyzer system also includes a temperature sensor for measuring a temperature of the gas in the cavity, and a pressure sensor for measuring a pressure of the gas in the cavity. In certain aspects, the detector system includes one of a photo-detector configured to measure an intensity of the intra-cavity light or both a photo-acoustic sensor configured to measure photo-acoustic waves generated in the cavity and a photo-detector configured to measure an intensity of the intra-cavity light.

According to another embodiment, a gas analyzer system is provided for measuring an isotopic ratio of a gas. The system typically includes a resonant optical cavity having two or more mirrors and containing a gas having a chemical species to be measured, the cavity having a free spectral range that equals the difference between frequencies of the measured absorption lines of two different isotopes divided onto an integer number, a continuous-wave tunable laser optically coupled to the resonant optical cavity, and a detector system for measuring an absorption of laser light by the gas in the cavity. In certain aspects, the gas analyzer system also includes a temperature sensor for measuring a temperature of the gas in the cavity, and a pressure sensor for measuring a pressure of the gas in the cavity. In certain aspects, the detector system includes one of a photo-detector configured to measure an intensity of the intra-cavity light or both a photo-acoustic sensor configured to measure photo-acoustic waves generated in the cavity and a photo-detector configured to measure an intensity of the intra-cavity light.

According to yet another embodiment, a system for measuring the isotopic ratio of a gas is provided. The system typically includes a resonant optical cavity containing a gas with chemical species to be measured and having a free spectral range equal to the difference between frequencies of the measured absorption lines of different isotopes divided onto an integer number, and a continuous-wave tunable coherent light source, such as a laser, optically coupled to the resonant optical cavity. The system also typically includes a detector for measuring an absorption coefficient. In one embodiment, the detector includes a photo-detector for measuring the intensity of the intra-cavity light. The system also typically includes a temperature sensor for measuring the temperature of the analyzed gas, and a pressure sensor for measuring the pressure of the analyzed gas.

According to a further embodiment, a method is provided for performing an absorption measurement. The method can be implemented in a system described above, or in a different system. The method typically includes selecting absorption lines of different isotopes having equal or close quantum numbers, for example dn=-2, 0, +2, or dn=-2, -1, 0, +1, +2, or dn=-1, 0, +1, and tuning a cavity mode to a first wavelength corresponding to an absorption line of one of the isotopes. The method also typically includes generating light having the first wavelength corresponding to an absorption line of one of the isotopes, measuring a first signal representing an absorption coefficient for the first wavelength, e.g., measuring a signal corresponding to the intra-cavity optical power at the first wavelength, tuning a cavity mode to a second wavelength corresponding to an absorption line of the second isotope, generating light having the second wavelength corresponding to an absorption line of the second isotope and measuring a second signal representing an absorption coefficient for the second wavelength, e.g., measuring a signal corresponding to the intra-cavity optical power at the second wavelength. The method also typically includes calculating an isotope ratio based on the first and second measured signals. In certain aspects, a baseline is defined or determined by measuring an absorption coefficient at a wavelength that does not correspond with an absorption line of any of the isotopes being measured or analyzed.

According to another embodiment, a method is provided for performing an absorption measurement. The method can be implemented in a system described above, or in a different system. The method typically includes tuning a cavity mode to a first wavelength corresponding to an absorption line of a first one of at least two different isotopes that have equal or close quantum numbers, generating light comprising the first wavelength corresponding to an absorption line of the isotopes, and measuring a signal corresponding to an absorption coefficient at the first wavelength. The method also typically includes tuning a cavity mode to a second wavelength corresponding to an absorption line of a second isotope, generating light comprising the second wavelength corresponding to an absorption line of the second isotope, and measuring a signal corresponding to an absorption coefficient at the second wavelength. The method also typically includes calculating the isotope ratio based on two measured signals. In certain aspects, a baseline is defined or determined by measuring an absorption coefficient at a wavelength that does not correspond with an absorption line of any of the isotopes being measured or analyzed.

According to yet a further embodiment, a method is provided for performing an absorption measurement. The method can be implemented in a system described above, or in a different system. The method typically includes selecting absorption lines of different isotopes that have equal or close quantum numbers, e.g., dn=2, 0, +2, or dn=-2, -1, 0, +1, +2, or dn=-1, 0, +1, and selecting or adjusting the cavity length such that the difference between frequencies of the measured absorption lines of different isotopes is a product of an integer number and the cavity free spectral range. The method also typically includes tuning a cavity mode to a wavelength corresponding to an absorption line of one of the isotopes, generating light having a first wavelength corresponding to an absorption line of one of the isotopes, and measuring a signal representing an absorption coefficient for the first wavelength, e.g., measuring a photo-acoustic signal and/or measuring a signal corresponding to the intra-cavity optical power at the first wavelength. The method also typically includes generating light having a second wavelength corresponding to an absorption line of the second isotope, and measuring a signal representing an absorption coefficient for the second wavelength, e.g., measuring a signal corresponding to the intra-cavity optical power at the second wavelength. The method also typically includes calculating an isotope ratio based on the measured signals. In certain aspects, a baseline is defined or determined by measuring an absorption coefficient at a wavelength that does not correspond with an absorption line of any of the isotopes being measured or analyzed.

According to a further embodiment, a method is provided for performing an absorption measurement. The method can be implemented in a system described above, or in a different system. The method typically includes selecting absorption lines of different isotopes that have equal or close quantum numbers, e.g., dn=2, 0, +2, or dn=-2, -1, 0, +1, +2, or dn=-1, 0, +1, and selecting or adjusting a cavity length such that the difference between frequencies of the measured absorption lines of different isotopes is a product of an integer number and the cavity free spectral range. The method also typically includes tuning a cavity mode to a wavelength corresponding to an absorption line of one of the isotopes, generating light having a first wavelength corresponding to an absorption line of a first one of the isotopes, and generating light having a second wavelength corresponding to an absorption line of a second isotope. The method also typically includes measuring signals representing absorption coefficients for the first and second wavelengths, e.g., measuring photo-acoustic signals and/or measuring signals corresponding to the intra-cavity optical power at the first and second wavelengths, and calculating an isotope ratio based on the measured signals. In certain aspects, a baseline is defined or determined by measuring an absorption coefficient at a wavelength that does not correspond with an absorption line of any of the isotopes being measured or analyzed.

In certain aspects, measurements of absorption of the gas mixture are made not only at wavelengths corresponding to absorption lines of isotopes, but at other wavelengths, for example, where there is no absorption. This can be useful to determine or define a baseline. For example, measuring only two peak intensities for two isotopologue lines may not be sufficient, and at least one more measurement in the area that does not belong to any of the two absorption lines may be needed. Such a measurement gives the information about the baseline.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

The present invention relates generally to trace gas detection and more specifically to cavity enhanced absorption spectroscopy systems and methods. Such systems and methods are useful for measuring the isotope ratio of trace gases and components of gas mixtures. Systems and methods for detecting trace gases according to various embodiments utilize a resonance optical cavity and a coherent light source coupled to the cavity, and provide improved accuracy and stability as compared to existing systems and methods based upon similar principles.

Figure 3A:
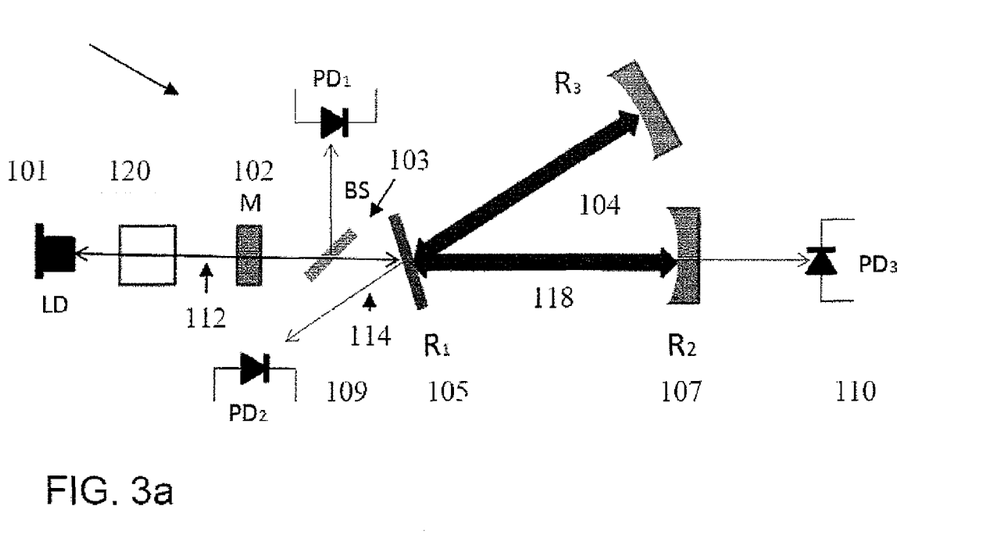
FIGS. 3a and 3b illustrate exemplary CEOS systems according to different embodiments.

FIG. 3a illustrates an exemplary cavity enhanced optical spectroscopy (CEOS) system 100 according to one embodiment. As shown, CEOS system 100 includes a light source 101 that emits continuous wave coherent light, such as continuous wave laser light, an optical cavity 104 and a detector system configured to measure absorption within the cavity, and hence an absorption coefficient, as well as other characteristics of incident and/or reflected light. In one embodiment, the detector system includes detector 110, however, the detector system may also include optional detectors 108 and/or 109. As shown, cavity 104 is a V-shaped cavity defined by cavity coupling mirror 105 and mirrors 106 and 107. An optional enclosure or housing (not shown) provides an air tight seal for cavity 104 such as to allow control of the environment within the housing and hence the cavity 104. Enclosed cavities are desirable for certain applications. One or more optical components (M) 102 are configured and arranged to facilitate directing, and mode matching laser light from source 101 to the optical cavity 104 via cavity coupling mirror 105. In the embodiment shown in FIG. 3a, an optional beam splitting element 103 is positioned and aligned so as to allow substantially all of the incident light 112 emitted or generated by source 101 to impinge on cavity coupling mirror 105. A small portion of the incident light beam 112 is directed (e.g., reflected or refracted) by element 103 to optional detector 108, which can be used to measure the light incident on the cavity. Cavity coupling mirror 105, in this embodiment, is arranged at an angle with respect to beam 112 such that a portion of incident light 112 is reflected off of mirror 105 as reflected beam 114 and detected by optional detector 109. A portion of incident light 112 enters cavity 104 via mirror 105. Depending on the frequency of incident light 112 and the optical length of cavity 104 (e.g., optical length from mirror 107 to mirror 105 to mirror 106), light 118 circulating in the cavity 104 may build up and resonate at one or a plurality of cavity modes (cavity resonances evenly separated in frequency; commonly known as the FSR or free spectral range of the cavity). A small portion of the intracavity light 118 circulating in cavity 104 between mirror 107, 105 and 106, emerges or escapes via mirror 107 and also mirrors 106 and 107 as determined by their transmissivity. The light escaping mirror 105 impinges on element 103, which allows a small portion 120 to pass back to source 101, e.g., for optical feedback. In certain aspects, light returning to source 101 passes through optional phase control and/or attenuation elements 120, which advantageously provides for phase and/or intensity control of the optical feedback provided to source 101 from cavity 104. Examples of useful elements 120 might include an electro-optic modulator that imposes a modulation on the phase of the light and an attenuation element such as a Faraday rotator.

Figure 6:
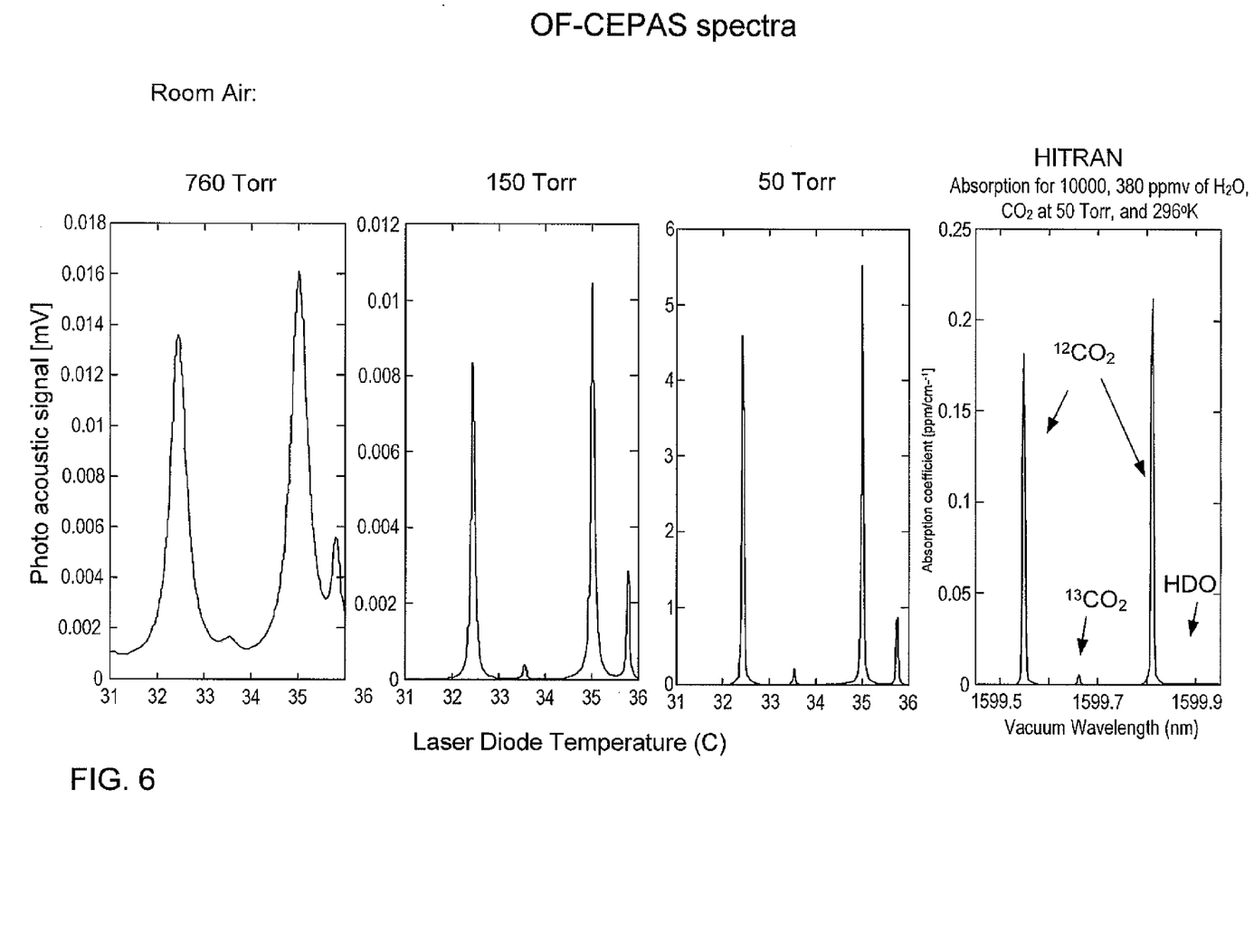
FIG. 6 illustrates photo-acoustic signals taken at different pressures, and also a HITRAN comparison, for $^{13}C$ and $^{12}C$ isotopes of $CO_2$ according to an embodiment.

In certain embodiments, system 100 also includes a temperature sensor positioned and configured to measure a temperature of the gas within cavity 104 and a pressure sensor positioned and configured to measure a pressure of the gas within cavity 104. It should be appreciated that more than one temperature sensor may be used, and that more than one pressure sensor may be used. For example, a single temperature sensor may be used to determine a temperature internal to the cavity, or where gas is flowed through the cavity, for example, two temperature sensors may be used to determine a temperature at a gas inflow port and a gas exhaust port, from which a temperature of the gas in the cavity can be determined. In certain embodiments, particularly closed cell or closed cavity embodiments, the temperature and pressure of the gas in the cavity is controlled using a temperature control element and a pressure control element. Control of the ambient conditions, e.g., temperature and/or pressure, can be useful to help improve signal resolution and SNR. For example, FIG. 6 illustrates photo-acoustic signals taken at different pressures, and also a HITRAN comparison, for $^{13}C$ and $^{12}C$ isotopes of $CO_2$.

In certain aspects, source 101 includes a laser or other coherent light source that is sensitive or responsive to optical feedback and that emits radiation at the desired wavelength(s) or desired wavelength range(s). One useful laser is a semiconductor diode laser that is sensitive to optical feedback from light impinging on the laser from the cavity coupling mirror 105. Other laser sources might include diode lasers, quantum cascade lasers and solid state lasers. The reflectivities of mirrors 105, 106 and 107 define the optical feedback intensity. U.S. patent application Ser. No. 13/252,915, filed Oct. 14, 2011, which is incorporated herein by reference in its entirety, discloses laser based cavity enhanced spectroscopy systems including mirror optimization techniques. It should be appreciated that the mirror 105 through which the laser light enters the cavity has a power reflectivity coefficient $R_1$ close to, but less than, unity such that the quantity $T=1-R_1$ is in the range from $10^{-1}$ to $10^{-5}$. The other cavity mirror(s) should have a power reflectivity $R_2$ equal to or higher than $R_1$. Such high reflective mirrors will certainly have some residual transmission, even though it may be as low as a few or several ppm.

In certain aspects, source 101 is capable of being frequency scanned, whereby a mean optical frequency of the laser is adjustable or tunable over a range of frequencies. This can be accomplished as is well known, such as, for example, by adjusting the current applied to a diode laser and/or adjusting a temperature of the laser medium. In certain aspects, the cavity 104 is also capable of being frequency scanned, e.g., by changing or adjusting an optical length of the cavity, whereby an optical frequency of a cavity resonance peak is adjustable over a range of frequencies. Adjustment of the optical length of the cavity can include adjusting a relative position of one or more of the cavity mirrors (e.g., using a piezo element), and/or adjusting a pressure of the medium within cavity 104. An intelligence module or control module, such as a computer system, processor, ASIC or other control circuitry, is provided to enable automated control of the source frequency tuning or scanning and/or cavity optical length adjustment.

In certain embodiments, CEOS system 100 is useful for detecting isotopes or trace gases within a gas mixture present in the cavity 104. When the frequency of the incident light 112 emitted by source 101 approaches the frequency of one of the cavity modes, the incident light 112 entering the cavity 104 begins to fill the cavity to that mode and may lock to that cavity mode. The optical intensity of the light 118 circulating inside the resonance cavity reflects total cavity loss at the moment when the light frequency of incident light 112 coincides with the cavity mode transmission peak. The total cavity loss is a sum of the cavity mirror losses and losses caused by absorption by the medium present in the cavity, e.g., absorption caused by absorbing analyte species present in the gaseous or liquid medium in cavity 104. Examples of such species detectable by embodiments herein include $H_2O$, $N_2O$, $NO$, $NO_2$, $CO_2$, $CH_4$, various hydrogen, carbon, nitrogen and oxygen isotopes, and many others. The isotopes may have close quantum numbers, e.g., dn=−2, 0, +2, or dn=−2, −1, 0, +1, +2, or dn=−1, 0, +1, For carbon isotopes of $CO_2$, for example, the lines are defined by even numbers, so the difference between two adjusted lines is +/−2.

In various embodiments, detector 110 is configured take measurements from which an absorption coefficient can be determined, e.g., based on measuring the intracavity optical power with and without an absorbing species present. For example, the power circulating inside the cavity ($P_{circ}$) is determined by the equation $P_{transm}=*T$, where T is the transmissivity of the mirror from which the light is escaping, and $P_{transm}$ is the power detected by the detector. In FIG. 3, detector 110 is shown proximal to mirror element 107, however, it should be appreciated that detection element 110 can be positioned to detect and measure the light escaping from mirror element 106 or mirror element 105 (e.g., reflected off of the backside of beamsplitter (BS)). Also, detection element 110 could be configured and positioned internal to the cavity 104 to measure the intracavity optical power. In certain embodiments, each detector element (e.g., elements 109 and 110) includes a photodetector, such as a photodiode, and associated electronics, for detecting light and outputting a signal representing the detected light. Examples of useful photodetectors might include silicon, InGaAs, Ge or GAP based photodetectors. Other useful detectors include CCDs, photomultipliers, etc. An intelligence module (e.g., a computer system, processor, ASIC or other control circuitry; not shown) receives the detector output signals and processes these signals to produce or generate a signal that characterizes the cavity loss based on the detection methodology used, e.g., PAS, free decay rate, phase shift, direct absorption, etc. For example, U.S. patent application Ser. No. 13/218,359, filed Aug. 25, 2011, which is incorporated herein by reference in its entirety, discloses laser based cavity enhanced spectroscopy systems including techniques for producing normalized signals that are a linear function of total cavity loss and that are not sensitive to laser-cavity coupling.

Figure 3B:
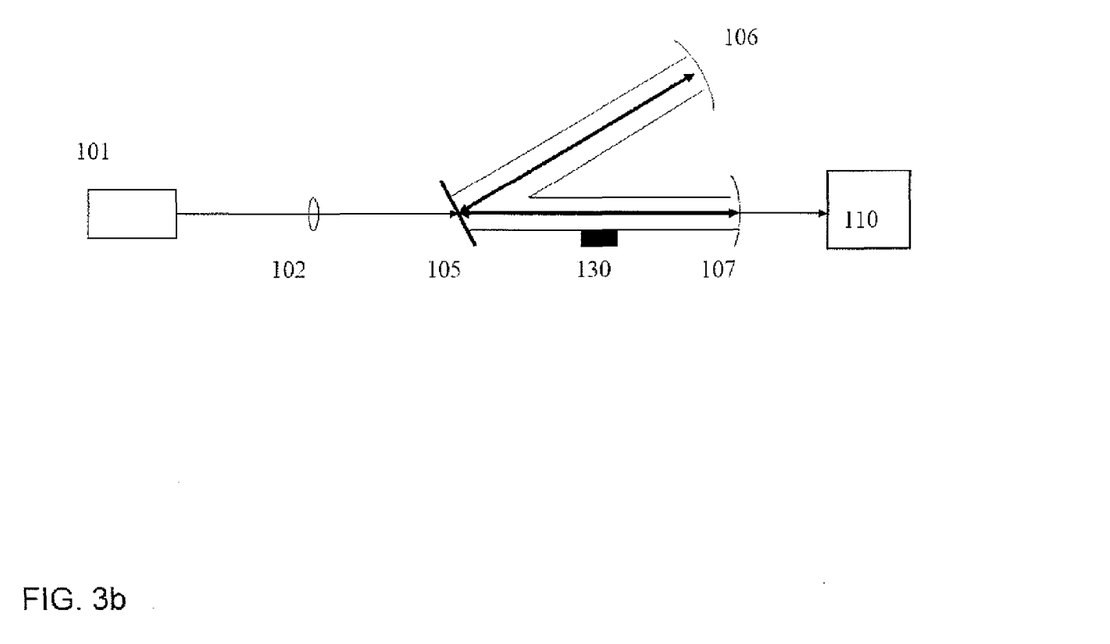

Additionally, as mentioned above, other detection methods can be used, for example, cavity ring-down spectroscopy methods, or cavity enhanced photo-acoustic spectroscopy (PAS) methods (see, e.g., U.S. patent application Ser. No. 12/660,614, (US Published Patent application 2011-0214479 A1) filed on Mar. 2, 2010, entitled "METHOD AND APPARATUS FOR THE PHOTO-ACOUSTIC IDENTIFICATION AND QUANTIFICATION OF ANALYTE SPECIES IN A GASEOUS OR LIQUID MEDIUM", the contents of which are hereby incorporated by reference). For example, FIG. 3b shows system 100 configured as a CE-PAS system including a photo-acoustic sensor 130 according to one embodiment. Source 101 emits illumination at the desired wavelength. The emitted radiation is mode matched to the cavity (defined by mirrors 104, 105 and 106) by mode matching optics 102 and enters the cavity via cavity coupling mirror 104. In one embodiment, the detector system includes a detector 107 that measures the intensity of intracavity optical power emerging from mirror 106 and a photo-acoustic detector 130, such as a quartz tuning fork or other photo-acoustic transducer, that measures photo-acoustic waves generated within the cavity. Measurements made by the detector system are used to determine an absorption coefficient for any gas species or isotopes present in the cavity. For CRDS measurements, the ring-down decay time is measured and used to determine the absorption coefficient.

Additionally, FIGS. 3a and 3b illustrate three mirror V-shaped cavities, however, it should be understood that the optical cavity could be a linear cavity including two or more mirrors, a ring cavity including three or more mirrors, or the cavity may take on any other configuration as may be apparent to one skilled in the art.

The methods described herein advantageously provide excellent accuracy with PAS methods in contrast to the common opinion of the reduced accuracy of PAS. Usually photo-acoustic methods are known to give less precise information about the absorption coefficient, because the PAS effect depends on the presence in the gaseous sample of some uncontrolled components, such as for example moisture or other gases. In this case, the impact of the presence of other gases will be the same for several isotopologues, and it will thus cancel out. Also, because PAS is a zero baseline method, PAS may offer higher accuracy than other methods. Moreover, even if the same or close quantum numbers are not used for different isotopologues, a PAS-based detection method will provide good results, because the impact of the gas composition will still be close for all isotopic species.

In certain embodiments, the frequencies of the cavity modes are advantageously controlled so that specific gas/isotope absorption lines match up with cavity resonance peaks. In certain aspects, although the FSR is generally fixed, frequencies of the cavity modes are controlled by adjusting the optical cavity length. The optical cavity length can be adjusted by adjusting the cavity mechanical length, which can be done by moving at least one of the cavity mirrors, or by changing the cavity body temperature or by changing the cavity gas pressure.

Figure 4:
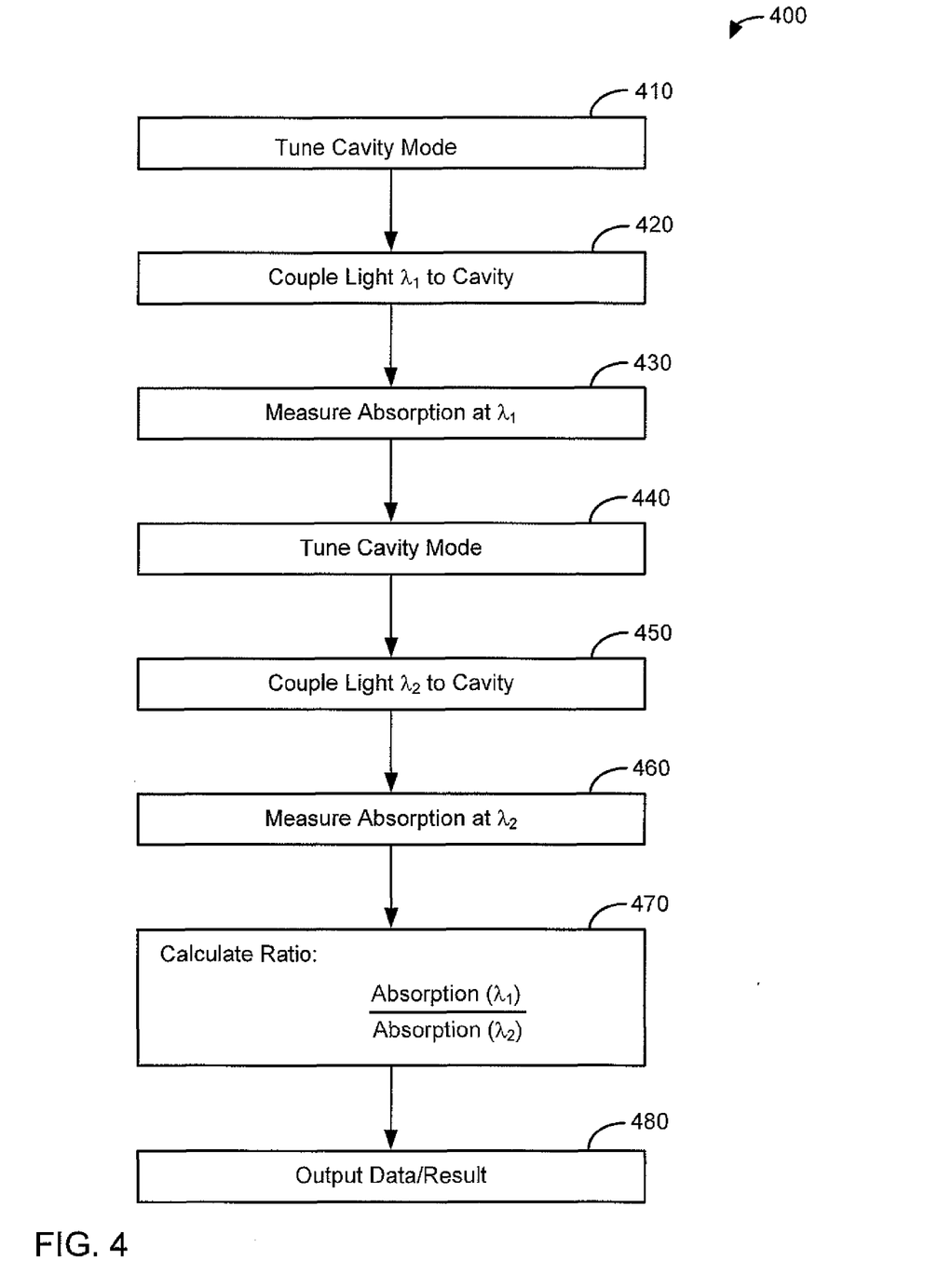
FIG. 4 illustrates a method of performing an absorption measurement according to one embodiment.

FIG. 4 illustrates a method 400 of performing an absorption measurement according to one embodiment. The absorption measurement method 400 may be performed using system 100 of FIG. 3 or other cavity system. In step 410, a cavity mode is tuned to a desired wavelength. For example, in embodiments where two different isotopes, including different isotopes having close or equal quantum numbers, are being measured, the cavity mode is tuned to a first wavelength corresponding to a known absorption line of first one of the two isotopes. Tuning the cavity mode in certain aspects includes adjusting a length of the cavity, e.g., by adjusting a position of one or more mirrors defining the cavity, so that the cavity has a resonance peak at the first wavelength. In step 420, light having the first wavelength is coupled with the cavity. For example, in certain aspects, the source (e.g., source 101) is adjusted or tuned to emit light at the first wavelength, and the emitted light is coupled with or injected into the cavity using mode matching optics as is well known. In step 430, a first absorption signal is measured using a detector. The detector may include a photo-detector, a photoacoustic sensor, or other detector as described herein or another detector to measure the intracavity optical power at the corresponding wavelength. The first absorption signal gives information from which an absorption coefficient is derived. For example, the absorption signal may be proportional to representative of the absorption coefficient of an isotope or gas species at the first wavelength.

In step 440, the cavity mode is tuned to a different desired wavelength. For example, in embodiments where two different isotopes having close or equal quantum numbers are being measured, the cavity mode is tuned to a second wavelength corresponding to a known absorption line of second one of the two isotopes. Tuning the cavity mode in certain embodiments includes adjusting a length of the cavity, e.g., by adjusting a position of one or more mirrors defining the cavity, so that the cavity has a resonance peak at the second wavelength. In step 450, light having the second wavelength is coupled with the cavity. For example, in certain aspects, the source (e.g., source 101) is tuned to emit light at the second wavelength, and the emitted light is coupled with or injected into the cavity using mode matching optics as is well known. In step 460, a second absorption signal is measured using a detector. The detector may include a photo-detector, a photoacoustic sensor, or other detector as may be described herein to measure the intracavity optical power at the corresponding wavelength. The second absorption signal gives information from which an absorption coefficient is derived. For example, the absorption signal may be proportional to representative of the absorption coefficient of an isotope or gas species at the second wavelength. In step 470, the first and second absorption signals are used to calculate the isotope ratio. Additional information such as gas pressure, gas composition, gas temperature and baseline absorption can also be used in such calculations as is well known. For example, an intelligence module, such as a computer system, processor, ASIC or other control circuitry, (not shown) receives the detector output signals and processes these signals to produce or generate the ratio, or to otherwise generate a signal that characterizes the cavity loss based on the detection methodology used. In certain aspects, step 470 is performed in real time, and in other aspects, step 470 is performed post data acquisition. In step 480, the result of step 470 is output or displayed (e.g., rendered on a display device or printed on viewable media). Alternatively, or additionally, the data (e.g., absorption at first wavelength and absorption at second wavelength) is output or displayed.

Figure 5:
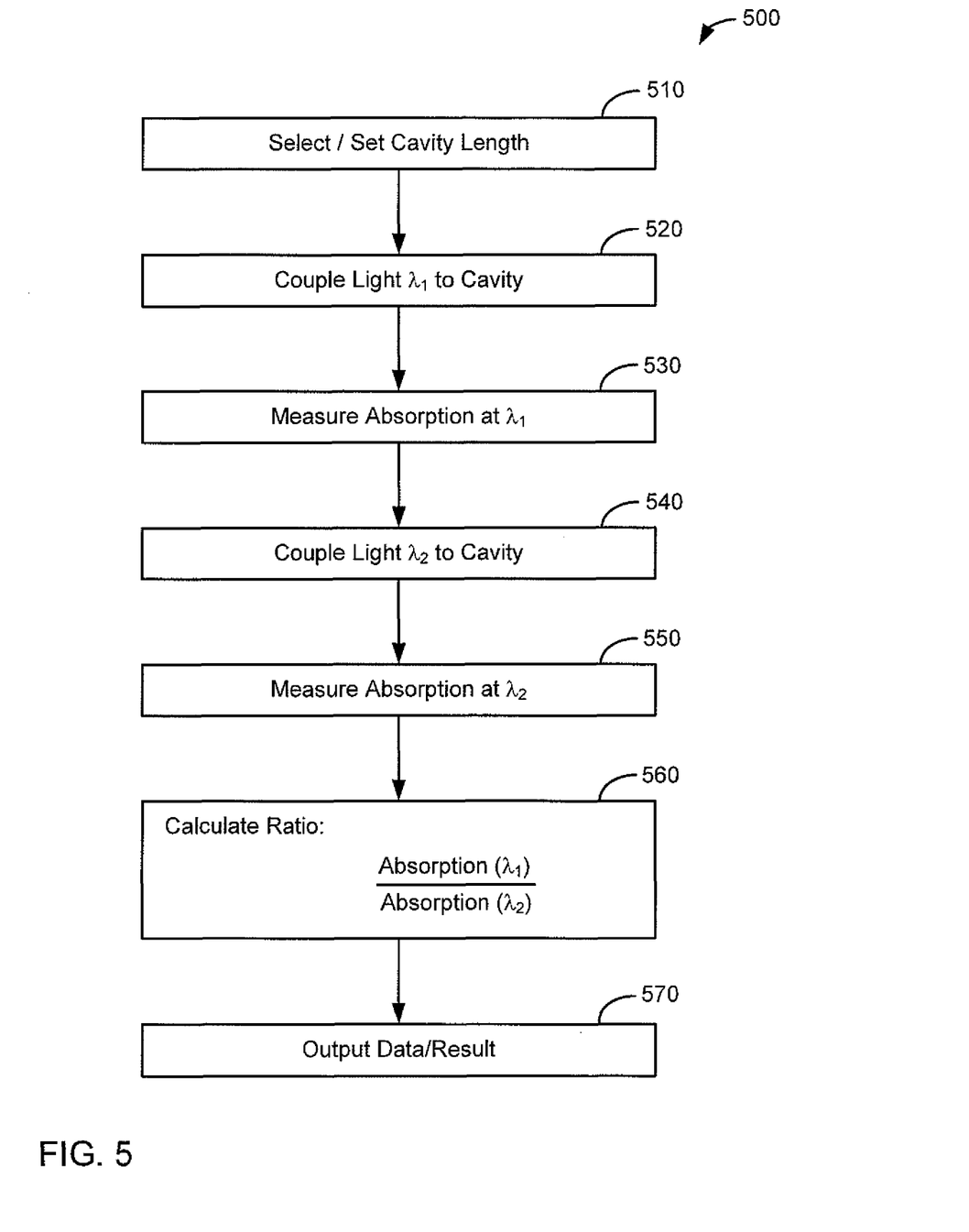
FIG. 5 illustrates a method of performing an absorption measurement according to another embodiment.

FIG. 5 illustrates a method 500 of performing an absorption measurement according to another embodiment. The absorption measurement method 500 may be performed using system 100 of FIG. 3 or other cavity system. In step 510, a cavity length is selected or set such that specific absorption line measurements for specific isotopes or gas species can be made, e.g., based on predetermined or known absorption lines depending on the desired gas species or isotopes to be measured. For example, in embodiments where two different isotopes are being measured, the cavity length is tuned or adjusted such that the free spectral range of the cavity is equal to the difference in frequency between absorption lines of the two isotopes divided by an integer number. In embodiments, where two different gas species are being measured, the cavity length is tuned or adjusted such that the free spectral range of the cavity is equal to the difference in frequency between absorption lines of the two gas species divided by an integer number. Selecting the length of the cavity by design can be done by adjusting a position of one or more mirrors defining the cavity. In step 520, light having a first wavelength corresponding to an absorption line/wavelength of a first one of the isotopes or gas species is coupled with the cavity. For example, in certain aspects, the source (e.g., source 101) is tuned to emit light at the first wavelength, and the emitted light is coupled with or injected into the cavity using mode matching optics as is well known. In step 530, a first absorption signal is measured using a detector. The detector may include a photo-detector, a photoacoustic sensor, or other detector as may be described herein to measure the intracavity optical power at the corresponding wavelength. The first absorption signal gives information from which an absorption coefficient is derived. For example, the absorption signal may be proportional to or representative of the absorption coefficient of the first isotope or gas species at the first wavelength.

In step 540, light having a second wavelength corresponding to an absorption line/wavelength of a second one of the isotopes or gas species is coupled with the cavity. For example, in certain aspects, the source (e.g., source 101) is tuned to emit light at the second wavelength, and the emitted light is coupled with or injected into the cavity using mode matching optics as is well known. In step 550, a second absorption signal is measured using a detector. The detector may include a photo-detector, a photoacoustic sensor, or other detector as may be described herein to measure the intracavity optical power at the corresponding wavelength. The second absorption signal gives information from which an absorption coefficient is derived. For example, the absorption signal may be proportional to or representative of the absorption coefficient of the second isotope or gas species at the first wavelength. In step 560, for isotopes, the first and second absorption signals are used to calculate the isotope ratio. For gas species, the first and signals are used to derive the absorption coefficients and/or concentration. Additional information such as gas pressure, gas composition, gas temperature and baseline absorption can also be used in such calculations as is well known. For example, an intelligence module, such as a computer system, processor, ASIC or other control circuitry, (not shown) receives the detector output signals and processes these signals to produce or generate the ratio, or to otherwise generate a signal that characterizes the cavity loss based on the detection methodology used. In certain aspects, step 560 is performed in real time, and in other aspects, step 560 is performed post data acquisition. In step 570, the result of step 560 is output or displayed. Alternatively, or additionally, the data (e.g., absorption at first wavelength and absorption at second wavelength) is output or displayed.

In certain aspects, the intelligence module such as a processor or computer system provides control signals to the various system components as necessary, and receives data and other signals from the various detectors and other components. It should be understood that the intelligence module could be a separate device or could be integrated with a spectroscopic analysis or gas analyzer system. It should also be understood that the intelligence module may be configured to merely collect and store the signals/data and that the collected signals/data may be transmitted to, sent to, or otherwise provided to a separate system that implements the signal/data processing and computation functionality described herein.

In some embodiments, a baseline is defined or determined by measuring an absorption coefficient at a wavelength that does not correspond with an absorption line of any of the isotopes or gas species being measured or analyzed. This is done in certain embodiments, by tuning the cavity to a mode that is resonant at a wavelength away from an absorption line and injecting an appropriate wavelength of light into the cavity. The baseline can be used in the methods 400 or 500 to produce a correct isotope ratio value, for example.

It should be appreciated that the various calculation and data processing processes described herein may be implemented in processor executable code running on one or more processors. The code includes instructions for controlling the processor(s) to implement various aspects and steps of the gas analysis processes. The code is typically stored on a hard disk, RAM or portable medium such as a CD, DVD, etc. The processor(s) may be implemented in a control module of a spectroscopic gas analysis system, or in a different component of the system such as gas analyzer having one or more processors executing instructions stored in a memory unit coupled to the processor(s). The processor(s) may be part of a separate system directly or indirectly coupled with the gas measurement system. Code including such instructions may be downloaded to the system or gas analyzer memory unit over a network connection or direct connection to a code source or using a portable, non-transitory computer-readable or processor-readable medium as is well known.

One skilled in the art should appreciate that the processes of the present invention can be coded using any of a variety of programming languages such as C, C++, C#, Fortran, VisualBasic, etc., as well as applications such as Mathematica which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A gas analyzer system for measuring a concentration of two or more gas species in a gas mixture, the system comprising:
   a resonant optical cavity having two or more mirrors having a set cavity length with a free spectral range that equals the difference between frequencies of two predetermined or known absorption lines of two different gas species to be measured divided onto an integer number;
   a continuous-wave tunable laser optically coupled with the resonant optical cavity;
   a detector system for measuring an absorption of laser light by the gas in the cavity at said two predetermined or known absorption lines;
   and
   an intelligence module comprising a processor adapted to determine the concentration of the two different gas species,
   wherein the laser is tuned to a first wavelength corresponding to a predetermined or known absorption line of a first one of the two gas species and the detector system measures a first signal corresponding to an absorption at the first wavelength, wherein the laser is tuned to a second wavelength corresponding to a predetermined or known absorption line of a second one of the two gas species and the detector system measures a second signal corresponding to an absorption at the second wavelength, and wherein the processor processes the first and second signals and generates an output signal representing concentrations of the first and second gas species.

2. The system of claim 1, further including;
   a temperature sensor for measuring a temperature of the gas in the cavity; and
   a pressure sensor for measuring a pressure of the gas in the cavity.

3. The system of claim 1, wherein the detector system includes a photo-detector configured to measure an intensity of the intra-cavity light.

4. The system of claim 1, wherein the detector system includes a photo-detector configured to measure an intensity of the intra-cavity light and a photo-acoustic sensor configured to measure photo-acoustic waves generated in the cavity.

5. The system of claim 1, wherein the laser is tuned to a third wavelength that does not correspond with an absorption line of any of the gas species being measured or analyzed, and wherein the detector system measures a third signal at the third wavelength and wherein the intelligence module is further adapted to determine a baseline based on the third signal.

6. A gas analyzer system for measuring an isotopic ratio of a gas species, the system comprising:
   a resonant optical cavity having two or more mirrors having a set cavity length with a free spectral range that equals the difference between frequencies of two predetermined or known absorption lines of two different isotopes of a gas species to be measured divided onto an integer number;

a continuous-wave tunable laser optically coupled to the resonant optical cavity;

a detector system for measuring an absorption of laser light by the gas in the cavity cavity at said two predetermined or known absorption lines; and an intelligence module comprising a processor adapted to determine an isotope ratio of the two different isotopes, wherein the laser is tuned to a first wavelength corresponding to a predetermined or known absorption line of a first one of the two isotopes and the detector system measures a first signal corresponding to an absorption at the first wavelength, wherein the laser is tuned to a second wavelength corresponding to a predetermined or known absorption line of a second one of the two isotopes and the detector system measures a second signal corresponding to an absorption at the second wavelength, and wherein the processor processes the first and second signals and generates an output signal representing an isotope ratio of the two different isotopes.

7. The system of claim 6, further including:
a temperature sensor for measuring a temperature of the gas in the cavity; and
a pressure sensor for measuring a pressure of the gas in the cavity.

8. The system of claim 6, wherein the detector system includes a photo-detector configured to measure an intensity of the intra-cavity light.

9. The system of claim 6, wherein the detector system includes a photo-detector configured to measure an intensity of the intra-cavity light and a photo-acoustic sensor configured to measure photo-acoustic waves generated in the cavity.

10. The system of claim 6, wherein the laser is tuned to a third wavelength that does not correspond with an absorption line of any of the isotopes being measured or analyzed, and wherein the detector system measures a third signal at the third wavelength and wherein the intelligence module is further adapted to determine a baseline based on the third signal.

11. A gas analyzer system for measuring concentrations of isotopes in a gas species, the system comprising:
a resonant optical cavity having two or more mirrors and having a set cavity length with a free spectral range that equals the difference between frequencies of two predetermined or known absorption lines of two different isotopes of the gas species to be measured divided onto an integer number;

a continuous-wave tunable laser optically coupled to the resonant optical cavity;

a detector system for measuring an absorption of laser light by the gas in the cavity cavity at said two predetermined or known absorption lines; and an intelligence module comprising a processor adapted to determine concentrations of the two different isotopes, wherein the laser is tuned to a first wavelength corresponding to a predetermined or known absorption line of a first one of the two isotopes and the detector system measures a first signal corresponding to an absorption at the first wavelength, wherein the laser is tuned to a second wavelength corresponding to a predetermined or known absorption line of a second one of the two isotopes and the detector system measures a second signal corresponding to an absorption at the second wavelength, and wherein the processor processes the first and second signals and generates an output signal representing concentrations of the first and second isotopes.

12. The system of claim 11, further including:
a temperature sensor for measuring a temperature of the gas in the cavity; and
a pressure sensor for measuring a pressure of the gas in the cavity.

13. The system of claim 11, wherein the detector system includes a photo-detector configured to measure an intensity of the intra-cavity light.

14. The system of claim 11, wherein the detector system includes a photo-detector configured to measure an intensity of the intra-cavity light and a photo-acoustic sensor configured to measure photo-acoustic waves generated in the cavity.

15. The system of claim 11, wherein the laser is tuned to a third wavelength that does not correspond with an absorption line of any of the isotopes being measured or analyzed, and wherein the detector system measures a third signal at the third wavelength and wherein the intelligence module is further adapted to determine a baseline based on the third signal.

* * * * *